United States Patent [19]

Haggag

[11] Patent Number: 4,852,397
[45] Date of Patent: Aug. 1, 1989

[54] FIELD INDENTATION MICROPROBE FOR STRUCTURAL INTEGRITY EVALUATION

[76] Inventor: Fahmy M. Haggag, 115 Clemson Dr., Oak Ridge, Tenn. 37830

[21] Appl. No.: 323,967

[22] Filed: Mar. 15, 1989

Related U.S. Application Data

[63] Continuation-in-part of Ser. No. 144,088, Jan. 15, 1988, abandoned.

[51] Int. Cl.$^4$ .............................................. G01N 3/42
[52] U.S. Cl. ....................................................... 73/82
[58] Field of Search ..................... 73/81, 82, 620, 624, 73/625, 629, 790, 794, 795, 799, 806, 807, 808, 813, 821

[56] References Cited

U.S. PATENT DOCUMENTS

| | | |
|---|---|---|
| 2,158,008 | 5/1939 | Grant, Jr. |
| 3,822,946 | 7/1974 | Rynkowski ............................. 73/81 |
| 3,879,982 | 4/1975 | Schmidt .................................. 73/82 |
| 4,199,976 | 4/1980 | Edward .................................. 73/81 |
| 4,294,118 | 10/1981 | Shiraiwa et al. ...................... 73/620 |
| 4,331,026 | 5/1982 | Howard et al. ........................ 73/81 |
| 4,433,582 | 2/1984 | Joosten ................................. 73/788 |
| 4,437,332 | 3/1984 | Pittaro .................................. 73/624 |
| 4,621,523 | 11/1986 | Shabel et al. .......................... 73/81 |
| 4,635,471 | 1/1987 | Rogers et al. .......................... 73/81 |
| 4,671,104 | 6/1987 | Fischer .................................. 73/81 |
| 4,699,000 | 10/1987 | Lashmore et al. ...................... 73/81 |
| 4,764,882 | 8/1988 | Braschel et al. ....................... 73/794 |

FOREIGN PATENT DOCUMENTS

| | | |
|---|---|---|
| 0843316 | 7/1952 | Fed. Rep. of Germany .......... 73/81 |
| 0201202 | 7/1983 | Fed. Rep. of Germany . |
| 0196439 | 11/1983 | Japan . |
| 1185248 | 10/1985 | U.S.S.R. . |

OTHER PUBLICATIONS

"The Use of Miniaturized Tests to Predict Flow Properties and Estimate Fracture Toughness in Deformed Steel Plates", by F. M. Haggag et al., ASM Proceedings of the Fracture-Mechanism Program of the International Conference and Exposition on Fatigue, Corrosion Cracking, Fracture Mechanics and Failure Analysis, 2-6 Dec. 1985, Salt Lake City, Utah, pp. 399-406.
"Determination of Luders Strains and Flow Properties from Hardness/Microhardness Tests", by F. M. Haggag and G. E. Lucas, Metallurgical Transactions A, vol. 14A, pp. 1607-1613.

Primary Examiner—Stewart J. Levy
Assistant Examiner—Robert R. Raevis

[57] ABSTRACT

Apparatus and methods for the in-field measurement of mechanical and physical properties of metallic structures. The apparatus is a Field Indentation Microprobe (FIM) using an indenter that is caused to contact and indent the structure using cyclically applied and released successive increasing loads at the same location. The load and penetration depth data during both cyclic loading and unloading are used to determine the flow properties and fracture toughness of the structure. An X-Y driven testing head supports a load cell which is connected to an indenter holder and the indenter. A displacement transducer is carried by the load cell to measure the depth of penetration of the indenter into the structure, and one or more ultrasonic transducers determine the physical phenomena such as crack size, material pile-up around indentation, and residual stress presence and orientation. A polishing tool is provided to prepare the surface of the structure prior to indentation. Also, a video camera is provided to view the surface, and to measure the final diameter of indentation. A data acquisition system and a computer appropriately programmed for automated testing and for acquiring and processing test data are used to provide the desired mechanical and physical property information. Accordingly, changes in local mechanical and physical properties of a structure, due to either normal service or damage, can be determined nondestructively in the field, and hence structural integrity can be evaluated.

13 Claims, 5 Drawing Sheets

FIELD INDENTATION MICROPROBE FOR STRUCTURAL INTEGRITY EVALUATION

This is a continuation-in-part patent application based upon patent application Ser. No. 144,088 filed Jan. 15, 1988, and now abandoned. The invention of this patent application was described in Disclosure Document No. 170,881 filed in the U.S. Patent and Tradement Office May 29, 1987.

TECHNICAL FIELD

This invention relates to methods and apparatus for measuring a combination of mechanical properties, specifically: the flow properties (true stress/true-plastic-strain curve), elastic (Young's) modulus, Lüders strain, strain-hardening exponent, and fracture toughness; and physical properties such as crack size, component thickness, and presence and orientation of residual stresses; in order to evaluate the structural integrity of metallic structures (e.g. pressure vessels and pipes, tank cars, bridges, aged aircraft, etc.), and more particularly to a device and its associated integrated equipment for principal use exterior to a testing laboratory, i.e., as an "in-the-field" system, that can be taken to the structure to be examined. Alternatively, the device and its associated equipment can be utilized in a testing laboratory.

BACKGROUND OF THE INVENTION

The invention was conceived as a solution to the problem of determining the integrity of deformed or otherwise damaged structures. It is equally applicable to determine the integrity of metallic materials subjected to nuclear radiation. The capability of the invention to measure accurately service-related changes in several mechanical properties has been demonstrated for both unirradiated and irradiated materials.

In order to assess the integrity of metallic structures following accidents or severe service conditions, knowledge of the material's mechanical properties (particularly flow properties and fracture toughness), the size and extent of induced defects or cracks, and the current thickness and residual stresses is required. This knowledge is particularly important for nuclear components such as pressure vessels and their supports because of the radiation-induced embrittlement.

In the case of derailed railroad tank cars carrying hazardous materials, the eventual cleanup operation requires assurance that moving and removing the derailed/damaged tank cars do not cause safety problems. In such a situation, the damage may cause the mechanical and physical properties to vary greatly over short distances, and accurate determination of these properties is needed to assess the structural integrity of damaged/deformed components. The other essential information: the size and extent of service- or damage-induced defects, and the current thickness (since appreciable decrease of material thickness reduces the load-carrying capability of the structure), can be determined by nondestructive test techniques such as ultrasonic inspection.

Presently the change in flow properties and fracture toughness might be obtained by performing tensile and fracture toughness tests on similar materials with simulated laboratory deformation/damage. Although this approach may be satisfactory in some instances, there are other circumstances where it might not be acceptable due to unknown component material or heat treatment condition. Furthermore, the applicability of results from simulated tests to determine the integrity of the actual deformed structure will always have some degree of uncertainty, and such an approach is very expensive. An article entitled "The Use of Miniaturized Tests to Predict Flow Properties and Estimate Fracture Toughness in Deformed Steel Plates" by F. M. Haggag et al., published by the American Society for Metals (ASM) in the Proceedings of the Fracture-Mechanism Program of the International Conference and Exposition on Fatigue, Corrosion Cracking, Fracture Mechanics and Failure Analysis, 2–6 Dec. 1985, Salt Lake City, Utah, pages 399–406, briefly describes this simulated testing approach as well as some of the problems in this area of testing.

Accurate determination of the flow properties and fracture toughness at the worst-damaged/deformed component location is essential for a complete and reliable fracture mechanics analysis in order to assure the safe operation of a metallic structure. Presently no other single in-field or laboratory device or technique exists that can obtain directly and accurately the wide range of mechanical and physical properties that the Field Indentation Microprobe (FIM) apparatus of this invention can measure. These properties include elastic (Young's) modulus, yield strength for all metallic materials including those exhibiting Lüders (inhomogeneous) strains, Lüders strain, strain-hardening exponent, actual material flow properties (true-stress/true-plastic-strain curve) up to 20% true-plastic-strain, fracture toughness, component thickness for determining allowable stress, thickness strains in deformed structural components, residual stress presence and orientation, crack identification and characterization, and creep. Furthermore, the mechanical properties can be measured at specified controlled strain rates and at a wide range of test temperatures, from a very small volume of the structure.

In contrast, some hardness test techniques such as the Rockwell hardness, or others using ball indenters, can be used to measure hardness only. Although sometimes these hardness numbers are converted to ultimate tensile strength values, such conversions are at best approximations and the American Society for Testing and Materials (Section 9.1 of ASTM Standard E 18-84) recommends that such conversions should be avoided. Furthermore, accurate conversion of such hardness numbers to yield-strength values, essential for fracture mechanics analysis and determination of a shift in the ductile-to-brittle transition temperature for steel plates and welds, can not be made. The FIM apparatus does not measure hardness, but instead measures a larger set of physical and mechanical properties, as will be explained later, and uses accurate and innovative techniques to reduce these measurements into meaningful information which is required to evaluate the integrity of the structure of interest.

The main problem in determining the yield strength from indentation tests is related to the Lüders strain behavior. In a uniaxial tensile test the Lüders strain is shown by the inhomogeneous plateau (horizontal portion) of the stress-strain curve and is confined mostly to a defined volume of the specimen gage section. Hence, the inhomogeneous (Lüders) and homogeneous (work hardening) plastic behaviors in a tensile test are well defined and separated from each other. In contrast, in an indentation test both occur simultaneously throughout the test because the material has less constraint at the surface around the indentation. With increasing loads, an increasing volume of material is forced to yield and flow under multiaxial compression caused by the indenter, and more material pile-up and Lüders strain occur around the indentation. Consequently, an accurate determination of the yield strength should be based on the entire load-displacement curve of the indentation test as explained later for the FIM testing. Lüders strain behavior in ball indentation testing is discussed and demonstrated in an article co-authored by the inventor and entitled "Determination of Lüders Strains and Flow Properties in Steels from Hardness/Microhardness Tests", published in Metallurgical Transactions A, Vol. 14A, pages 1607-1613 (August 1983). The technique reported in this article involved the use of a prior developed correlation (using either optical interferometry or mechanical profilometry techniques) between Lüders strain and the geometry of the lip (material pile-up) around a ball indentation, in order to determine the Lüders strain and then the yield strength for a certain carbon steel material. Since such a correlation for each material may not exist and its development is expensive, the FIM of this invention does not utilize such an approach. Furthermore, the use of optical interferometry is impractical for field testing application.

The present invention was conceived to incorporate innovative solutions to ten principal needs of in-situ nondestructive evaluation of structural integrity. The first is the in-field and nondestructive applicability. The second is the procedures which combine ease of field testing, simplicity, and computerized control of test procedure, data acquisition, and data analysis. The third is the automated measurement of material pile-up and geometry around the indentation. The fourth is the novel data acquisition/analysis techniques to measure, at a single location, the necessary material characteristics for subsequent property calculations. The fifth is the use of a very small material volume to measure properties nondestructively. The sixth is the adaptability to a wider variety of field and laboratory applications, e.g., weld inspection/qualification and new alloy evaluation. The seventh is the simulation of inservice structural loading conditions conveniently and more economically in laboratory or field. The eighth is the computer control of a motorized testing head to allow accurate positioning and use of adjacent ultrasonic transducers to determine material thickness and related changes caused by the testing procedure, crack presence and size, and presence and orientation of residual stresses. The ninth is the interchange to other appropriate indenter geometries for related types of testing such as indentation creep testing. The tenth is the use of both plastic and total (elastic plus plastic) indentation depth, as well as unloading curve slope, in test data analysis.

During the course of a preliminary patent search, the following patents were located: U.S. Pat. Nos. 2,158,008, issued to R. L. Grant, Jr. on May 9, 1939; 4,433,582, issued to M. W. Joosten on Feb. 28, 1984; German patentschrift No. 201-202; Russian Pat. No. 1185-248; and Japanese Pat. No. 58-196439.

Another reference that may be related to the present invention, due to computer control of testing using an indenter, is U.S. Pat. No. 4,621,523 issued to B. S. Shabel et al. on Nov. 11, 1986. In this patent the inventors thereof make the assumption that the diameter of impression does not change by elastic springback when the load on the indenter is removed (lines No. 11 and 12 of page 3 of the patent), thus ignoring the elastic recovery of the specimen. The applicant's approach in the present invention does not require this assumption. The patent of Shabel et al. further discusses obtaining hardness data at low and high strains and then relating the same to engineering yield and tensile strength values based upon empirical correlations between hardness and tensile data for a specific material. This material is aluminum in their case. Thus, the conversion of hardness data to engineering yield and tensile strength is not possible for unknown materials, new alloys, or welds. The FIM of this invention does not use such an approach or make such assumptions. The FIM of this invention measures the material flow properties by analyzing the elastic and plastic deformation during the cyclic loadings and unloadings of an indenter against a structure at the same indentation location. The analysis is based primarily on elastic and plastic theories. The FIM also accounts for the strain rate sensitivity of the test material while Shabel et al. do not. Indentation tests of the FIM are strain rate controlled via the use of an appropriately programmed computer and a data acquisition system, while Shabel's indentation tests are load controlled.

Shabel et al. do not take into account the fact that different materials behave very differently under uniaxial tensile loads. Some materials exhibit only a homogeneous plastic strain response, while others exhibit an initial non-homogeneous plastic behavior followed by a homogeneous response. The latter complex behavior is typical of most structural materials, such as carbon steels, aluminum alloys, titanium alloys, etc. Also, the material behavior under indentation tests will vary due to the presence of residual stresses that might result from accidental deformation or welding procedures. Relating hardness numbers from tests on these materials to yield strength values will not be successful.

In addition, Shabel et al. do not and can not measure flow properties (true-stress/true-plastic-strain curve up to 20% strain). The automated indentation test as disclosed and taught by the Applicant does measure these properties. The FIM of this invention provides a stress-strain diagram in which corresponding values of true-stress and true-plastic-strain are plotted against each other. The values of stress are plotted as ordinates (vertically) and values of strain as abscissa (horizontally). The true-stress/true-plastic-strain curve is particularly needed for the analysis of pipes and pressure vessels. Furthermore, the apparatus of Shabel et al. does not measure the elastic (Young's) modulus, strain-hardening exponent, Lüders strain, and fracture toughness of test materials. The numerous mechanical and physical properties measured by the FIM of this invention are discussed below.

Two other references, which deal only with hardness testing, are U.S. Pat. Nos. 4,199,976 issued to J. C. Edward on Apr. 29, 1980; and 4,635,471 issued to D. B. Rogers et al. on Jan. 13, 1987. There is no provision in either of these references as to the determination of any property other than hardness. Edward does teach magnet means for attaching the hardness apparatus to the material being tested, and Rogers et al. teaches cleaning of test area of pipe prior to testing (as known by others).

Other references showing the general art of hardness testing using an indenter probe are U.S. Pat. Nos. 4,671,104 issued to H. Fisher on June 9, 1987; 3,822,946 issued to G. A. Rynkowski on July 9, 1974; 4,331,026 issued to B. S. Howard et al. on May 25, 1982; and 3,879,982 issued to E. Schmidt on Apr. 29, 1975. None of the devices described in these patents provide information other than hardness; none can provide the broad information which is determined by the present invention.

Accordingly, it is an object of the present invention to provide an in-the-field and substantially nondestructive Field Indentation Microprobe (FIM) apparatus so as to measure, from load/displacement data during both loading and unloading, the yield strength, flow properties (true-stress/true-plastic-strain curve), strain hardening exponent, Lüders strain, elastic modulus, and fracture toughness of the concerned/actual component material, even when it is in a damaged, deformed, aged, or embrittled condition.

An additional object of the present invention is to provide a system that will determine the yield strength and the true-stress/true-plastic-strain curve for materials exhibiting only homogeneous (work hardening) strain behavior as well as those exhibiting both homogeneous and inhomogeneous (Lüders) strain behavior.

It is another object of the present invention to provide appropriate testing procedures for use with the field indentation microprobe (FIM) whereby accuracy, computerized test control and data acquisition and analysis are achieved.

It is also an object of the present invention to provide an in-the-field testing apparatus that can provide output information as to a wide variety of mechanical properties based upon the cyclic application (and release) of increasing loads to an indenter in contact with the surface of interest at a single location.

Another object of the invention is to provide means for measuring the amount and geometry of material pile-up around the indentation created by the indenter of the FIM in order to determine the presence and orientation of residual stresses in metallic materials and, alternatively, Lüders strain in materials such as low carbon steels, aluminum alloys, and titanium alloys, based on previously established correlations.

A further object is to provide apparatus which utilizes a very small surface area and volume of the structure under test and does not affect the integrity of that structure.

These and other objects of the present invention will become more apparent upon a consideration of the following drawings and a detailed description thereof.

BRIEF SUMMARY OF THE INVENTION

In the present invention, a microprobe system is provided for the in-field measuring of mechanical and physical properties, and determining the integrity of structures in situ. This system includes a computer-controlled motorized X-Y testing head that carries an indenter having means for the cyclic application and release of increasing loads at a given test location. The testing head is movable in an X-Y plane that is substantially parallel to the surface of the structure of interest. The head further carries a suitable displacement transducer for measuring movement of the indenter into and out of the specimen or structure. The system includes one or more ultrasonic transducers for measuring the thickness of the structure, any crack sizes, as well as the material pile-up around indentation after testing. A video camera is provided for viewing to verify the status of the test surface and measuring the final indentation geometry. Data from the load cell and from the displacement and ultrasonic transducers are processed by selected computer programs whereby information is generated as to the mechanical and physical properties of the specimen or the structure. These computer programs also control the cyclic application and release of the loads applied to the indenter. Various test operating limits are incorporated into the computer programs: interim and final indenter displacement and maximum indenter load. The apparatus and the methods are interdependent in operation, and use is effective only in combination. Although designed specifically for in-the-field applications, the present invention can also be used for laboratory investigations.

DESCRIPTION OF THE PREFERRED EMBODIMENTS

Figure 1:
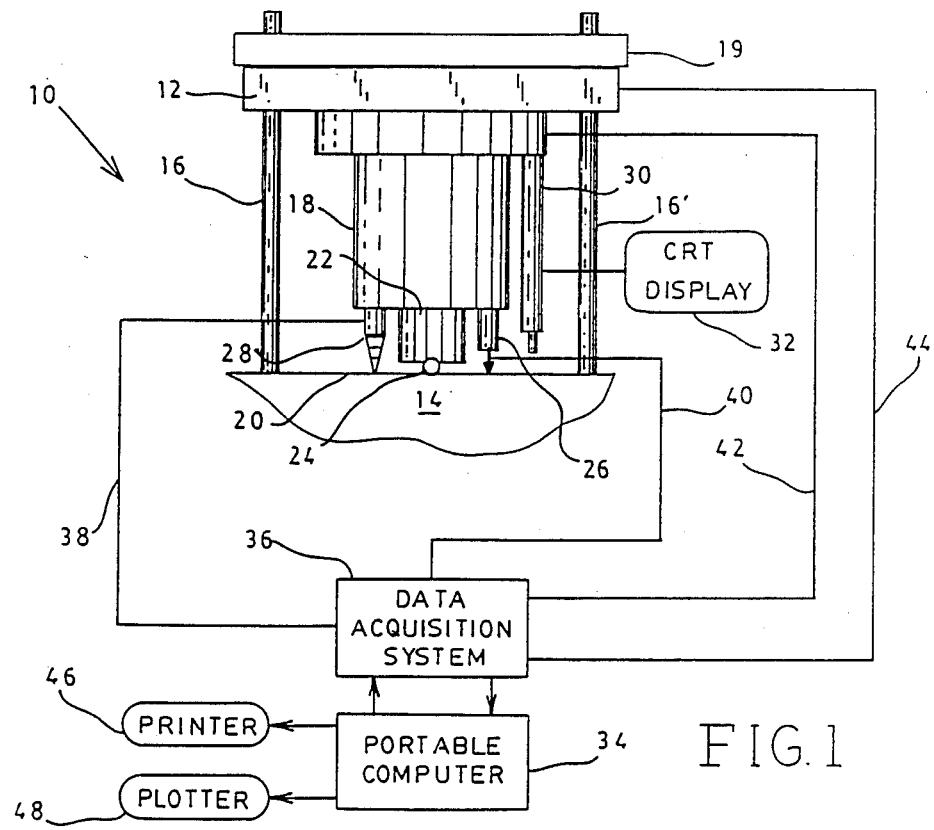
FIG. 1 is a schematic drawing illustrating the principal components of the present invention.

Referring first to FIG. 1, the essential components of the present invention are schematically shown at 10 therein A computer-controlled motorized testing head 12 is adapted for movement in the X and Y directions relative to a position above a structure 14 (the X-Y plane is substantially parallel to the surface of the structure under test). This head is releasably positioned relative to the structure by any suitable supports 16, 16' such that the operating components of a load cell or other load measuring means 18 can be moved perpendicularly with respect to the structure. Any conventional load-applying means 19 is operatively associated with the head 12 and the supports 16, 16'. Details of an exact mechanism 16, 16' for mounting the head 12 relative to the structure 14, and for the interrelationship of the load-applying means and the head, are not shown since the mechanisms will vary on a case-to-case basis depending upon the geometry and position of a particular structure. Also, many usable systems are well known in the art. Typically a tripod mechanism will be utilized having clamps, magnets, or the like for releasable attachment to the structure 14. A tripod arrangement facilitates adjustment of the orientation of the load cell 18 so as to be perpendicular to the surface 20 of the structure even if such surface is other than planar as illustrated. Thus, the head 12 can be moved in the X and Y directions in a plane substantially parallel to the surface of the structure.

The load cell 18 carries an indenter holder 22 having at its exposed end an indenter 24. Although any of the standard configurations of indenters can be used, such as diamond Vickers or Knoop, cylindrical, etc., a spherical or ball indenter is utilized in this embodiment. Typically the indenter and its holder are interchangeable so as to use one of three indenter sizes: 0.25 mm; 0.75 mm; and 1.50 mm diameter. Other sizes or geometries, of course, can be used. The indenter typically is fabricated from hardened steel, or for the testing of very hard materials, from tungsten carbide or the like. The holder 22 is moved axially by application of an appropriate load supplied by conventional load-applying means 19 such as hydraulic pressure, pneumatic pressure, screw driven, etc. The load cell also carries a displacement transducer 26 so as to measure the distance of penetration of the ball indenter into and out of the structure. This displacement transducer can be any one of a number of conventional instruments, such as a spring-loaded linear voltage differential transducer (LVDT), a capacitive transducer, etc. A resolving power of at least 0.001 mm is necessary together with a linear response over the full working distance (which depends upon the size of the ball indenter).

There is provided at least one, and usually two, ultrasonic transducers 28, 28' (see FIG. 2) of conventional design. These are used to scan the surface of the structure, using the movement of the head 12, in two nominally perpendicular directions for thickness measurements, to determine material pile-up around an indentation produced by the indenter, and detect and measure cracks and other defects. As will be known to those versed in the art, these ultrasonic transducers provide a reflected signal that is proportional to the thickness and/or crack size. Further, a video camera 30 is typically positioned near the load cell to view the area of the indentation to provide information as to the condition of the surface and measure the plastic diameter of the final indentation if desired. This camera is connected to a display 32. Although not shown, a videocassette recorder (VCR) can be used to record information as observed by the camera.

The field indentation microprobe of the present invention is fully automated using an appropriately programmed computer 34 and a data acquisition system 36. The data acquisition system receives and transmits signals via leads 38, 40, 42, and 44. Although shown as single leads, it will be understood by those versed in the art that each lead is actually a plurality of signal leads. The computer 34, which controls the load applying means 19 and processes the data from the data acquisition system 36, is typically any suitable personal, microtype or portable computer, and the details of a suitable data acquisition system will be known to those versed in the art when the data processing details, as described hereinafter, are established. The resultant data is typically presented using a printer 46 and/or plotter 48. Both the printer and plotter are of conventional design. The data can also be stored on magnetic or optical disks or the like associated with the computer for permanent records or for further post-test analysis.

Figure 2:
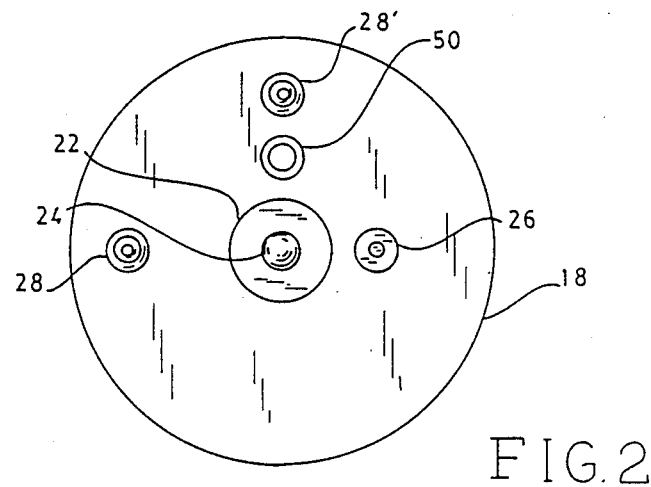
FIG. 2 is a drawing illustrating the placement positions of components carried by the face of the load cell of the system shown in FIG. 1.

The lower face of the load cell 18 is shown in FIG. 2. This illustrates typical positions for the ultrasonic transducers 28, 28' and the displacement transducer 26 with respect to the indenter 24 and its holder 22. Also shown is a tool 50 that is used to prepare the surface 20 prior to conducting any tests thereon. This preparation typically involves cleaning, smoothing and polishing so that surface conditions will not adversely affect the quality of the data being taken from that surface.

Figure 3:
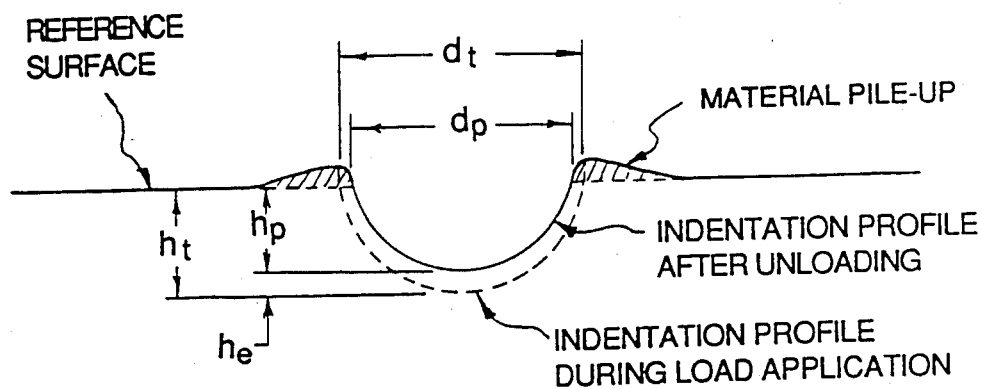
FIG. 3 is a drawing illustrating the pile-up of material at the edge of a depression (indentation) produced by a ball or spherical indenter of the present invention. This figure also illustrates the profile geometry of the indentation during loading (elastic plus plastic deformation) and after complete release of load (remaining plastic deformation after the elastic recovery of test material).
Figure 4:
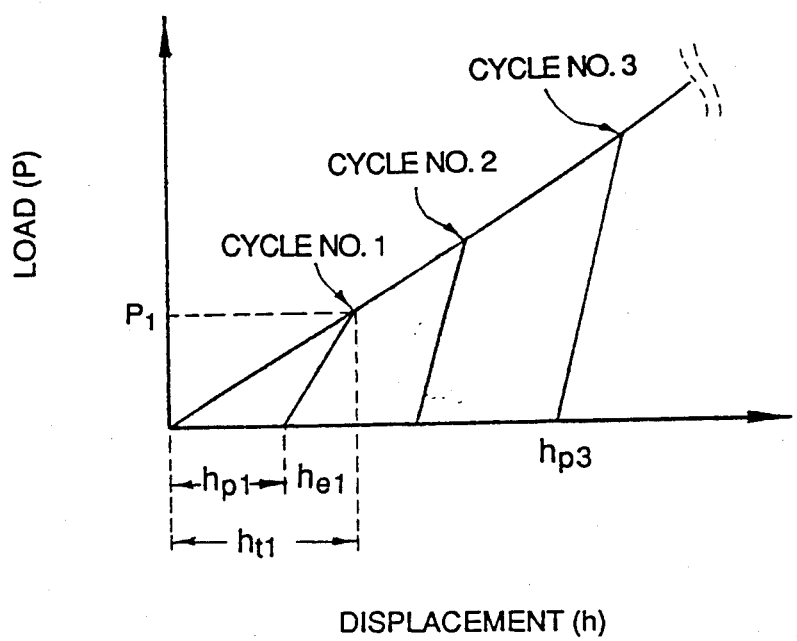
FIG. 4 is a graphical representation of the relationship between load and displacement of the indenter of FIG. 1 as observed by successive (cyclic) application and release of increasing indentation loads to a given material at the same single test (penetration) location.

The principle of operation of an indenter system such as in the present invention can be better understood by reference to FIGS. 3 and 4. Referring first to FIG. 3, when the indenter (of FIG. 1) is forced (under control by the computer) into the nominal surface of a structure, an indentation is formed whose size is dependent upon the size of the indenter, the applied indentation load, and the flow properties of the test material. Not only an indentation is produced, but a ring of material pile-up is formed around the indentation. Large material pile-up due to Lüders strain is frequently observed during testing of low carbon steels and other materials such as aluminum alloys, titanium alloys, etc. Also, residual stresses in the structure can result in a nonsymmetrical pile-up of the material. As shown schematically in FIG. 3, the total indentation depth, $h_t$, while the load is applied is a result of elastic and plastic deformation of the test material, and it is greater than the plastic indentation depth, $h_p$, when the load is completely removed due to the elastic recovery (springback) of the test material (note that $h_t = h_p + h_e$, where $h_e$ is the elastic indentation depth). Similarly, the indentation total diameter, $d_t$ while the load is applied is greater than the plastic indentation diameter, $d_p$, when the load is removed.

The indentation geometry changes as the indenter is subjected to cyclic loading (i.e., application of load followed by at least partial release of the load), with the load increasing with each successive cycle. The typical results of such cyclic loading (followed by complete unloading) are illustrated in FIG. 4. When a load, $P_1$, is applied during the first cycle, the respective displacements are $h_{t1}$ during loading, and $h_{p1}$ when the load is removed completely. Subsequent higher loadings at the same test location produce the increasing values of $h_t$ and $h_p$ as shown in FIG. 4. From the knowledge that the unloading curve is essentially linear and a comparison of test results using both complete unloading (as illustrated in FIG. 4) and partial unloading (as shown later in FIG. 5), it has been determined that accurate results can be obtained using only partial unloading. The computer program used to control the test and analyze test data calculates the slope of each unloading cycle and then the intersection of this line with the zero load line (abscissa or X-axis) to determine the plastic indentation depth, $h_p$.

The present field indentation microprobe is utilized in the following manner. After the testing head 12 is properly secured to the structure to be tested so that the load cell is perpendicular to the surface of the region where testing is to be performed, this surface is prepared using, for example, the polishing tool 50. Thereafter, the computer, through use of the capability of the head, causes the indenter tip to be brought into contact with the polished surface. The total and plastic indentation depths ($h_{t1}$ and $h_{p1}$) and the applied indentation load ($P_1$) are then measured for the first cycle. Typically the load is increased for each succeeding cycle and the values of P, $h_t$, and $h_p$ are measured for each cycle. Several load cycles (typically five or more) are conducted at the same indentation location for determining a full true-stress/true-plastic-strain curve at this location (data from each cycle yield a point on this curve). This cyclic loading can be continued; however, the maximum total indentation depth ($h_t$) should not exceed one half of the diameter, D, of the indenter. Following the final cycle the plastic indentation diameter, $d_p$, can be independently measured using the video camera. If a measure of the amount of material pile-up and/or existence and orientation of residual stresses is required, thickness measurements are performed before and after indentation using the ultrasonic transducers 28, 28' over a traverse distance of at least one indenter diameter from each side of the indentation and in two nominally perpendicular directions. As stated above, the FIM operation is typically controlled by a program stored in the computer, and data as to the load, indentation depth, etc., measured using the data acquisition system are stored on magnetic or optical media in the computer for processing as discussed hereinafter.

The utility of the present invention stems in part from its ability to derive, from depth-of-penetration and load values obtained during cyclic and incremental loading and unloading, the essential material condition behavior. These include: true-stress/true-plastic-strain curve, strain-hardening exponent, strength coefficient, elastic (Young's) modulus, yield strength, Lüders strain, and fracture toughness.

In the present invention, the homogeneous plastic flow portion of the true-stress ($\sigma_t$)/true-plastic-strain ($\epsilon_p$) curve is represented by the familiar power law equation:

$$\sigma_t = K \epsilon_p^n \quad (1)$$

where
n = strain-hardening exponent
K = strength coefficient

An appropriate program stored in the computer 34 is used to solve the following equations and to thereby determine the flow curve from the Automated Ball Indentation (ABI) data.

$$\epsilon_p = 0.2 \, d_p/D \quad (2)$$

$$\sigma_t = 4P/\pi d_p^2 \delta \quad (3)$$

where $$d_p = \{0.5 \, CD[h_p^2 + (d_p/2)^2]/[h_p^2 + (d_p/2)^2 - h_pD]\}^{\frac{1}{3}} \quad (4)$$

$$C = 5.47P(1/E_1 + 1/E_2) \quad (5)$$

$$\delta = \begin{cases} 1.12 & \phi \leq 1 \\ 1.12 + \tau \ln\phi & 1 < \phi \leq 27 \\ \delta_{max} & \phi > 27 \end{cases} \quad (6)$$

-continued $$\phi = \epsilon_p E_2/0.43\sigma_t \quad (7)$$

$$\delta_{max} = 2.87\alpha_m \quad (8)$$

$$\tau = (\delta_{max} - 1.12)/\ln(27) \quad (9)$$

In the above equations, $\sigma_t$ is the true stress, $\epsilon_p$ is the true-plastic-strain, $d_p$ is the plastic indentation diameter, D is the diameter of the ball indenter, P is the applied indentation load, $h_p$ is the plastic indentation depth, $E_1$ is the elastic modulus of the indenter, $E_2$ is the elastic modulus of the test material, $\delta$ is a parameter whose value depends on the stage of development of the plastic zone beneath the indenter, $\alpha_m$ is a parameter proportional to the strain rate sensitivity of the test material or specimen (e.g., for low strain-rate-sensitive materials $\alpha_m = 1.0$), and "ln" is the natural logarithm.

The computer program is used to fit the ABI-derived $\sigma_t - \epsilon_p$ data (calculated using Equations 2 and 3) by linear regression analysis to the relationship of Equation (1), and determine the strain-hardening exponent (n) and the strength coefficient (K). The previous equations provide means for predicting the homogeneous portion of the stress/strain curve from indentation data.

A different approach must be used for measuring the yield strength of carbon steels (and other materials such as aluminum and titanium alloys) exhibiting inhomogeneous or Lüders strain. Similarly, methods of the prior art wherein the Lüders strain and yield strength are determined using either a profilometry or an optical interferometry technique, while suitable for laboratory applications, are not suitable for in-field applications because of their complexity.

In contrast, the information obtained using the FIM apparatus described above can be more easily and accurately used to obtain the yield strength of the test material using the following approach. For each ABI loading cycle the total penetration depth ($h_t$) is measured while the load is being applied, then converted to a total indentation diameter ($d_t$) using the following equation:

$$d_t = 2(h_tD - h_t^2)^{0.5} \quad (10)$$

Data points from all loading cycles up to $d_t/D = 1.0$ are fit by linear regression analysis to the following relationship:

$$P/d_t^2 = A(d_t/D)^{m-2} \quad (11)$$

where P is the applied indentation load, m is Meyer's coefficient, and A is a test material (or specimen) parameter obtained from the regression analysis of test data of $d_t/D$ versus $P/d_t^2$. The test material parameter (A) is then used to calculate the yield strength ($\sigma_y$) of the material using the following equation:

$$\sigma_y = \beta_m A \quad (12)$$

where $\beta_m$ is a material-type constant (e.g., a single value of $\beta_m = 0.2285$ is applicable to all carbon steels whether cold rolled, hot rolled, or irradiated; other values of $\beta_m$ for other types of material such as titanium alloys, aluminum alloys, etc. are stored in the computer). The value of $\beta_m$ for each class or type of material is determined from regression analysis of tensile yield-strength values (measured from specimens with different heat treatments and flow properties and machined from different orientations) and their corresponding "A" values as measured from entire ABI curves (up to $d_t/D=1.0$). In Equation (12) above, the units of A and $\sigma_y$ should be the same. The simplified and more accurate approach of this invention to determine yield strength eliminates the determination of material pile-up except for residual stress evaluation and thereby significantly reduces testing time and thus cost.

A further feature and advantage of the present field indentation microprobe is the measurement of material pile-up around the last (or final) indentation of any test location using the two ultrasonic transducers in two nominally perpendicular paths whereby thickness measurements are made before and after indentation. The material pile-up, of course, affects these thickness measurements. The scan paths cover at least one ball diameter from each side of the indentation. The presence of residual stresses in the structure under test will result in non-symmetrical material pile-up (e.g., the material pile-up will be higher in the direction of tensile residual stress). This manner of measuring the material pile-up is less complicated than prior art profilometry or optical interference methods and thus is more appropriate for in-the-field application. If the present invention is to be used in a laboratory an optical interference unit can be added.

The inhomogeneous (or Lüders) strain ($\epsilon_L$) can be determined from ABI tests of the present invention using the following equation:

$$\ln(K/\sigma_y) = \epsilon_L - n \ln \epsilon_L \tag{13}$$

where "ln" is the natural logarithm, $\sigma_y$ is the yield strength calculated from indentation data using Equation (12), K is the strength coefficient, and n is the strain-hardening coefficient calculated from indentation data as explained above. Again, this method of determining the Lüders strain is easier and faster than prior art methods of measuring material pile-up and then estimating the Lüders strain using previously established relationships between values of Lüders strain from tensile tests and material pile-up from indentation tests (conducted using a specific indenter at a specific load).

Although values of the elastic (Young's) modulus for many materials are available in the open literature, such data for new alloys sometimes do not exist. The elastic modulus of the test material, $E_2$, can be determined, using the subject field indentation microprobe, from the load, P, plastic indentation depth, $h_p$, and the plastic indentation diameter, $d_p$, as measured by the video camera, and the use of aforementioned Equation (4). Also the unloading slope of any cycle on the load-displacement curve of FIG. 4 can be used as a measure of the elastic properties of the test material.

The present invention provides a method to determine the shift in ductile-to-brittle transition temperature ($\Delta T$) for steel plates and welds, e.g., due to neutron irradiation embrittlement, from indentation testing. The relationship used is $$\Delta T = b \Delta \sigma_y \tag{14}$$

where b is a material-type coefficient obtained from available open literature correlations between tensile and Charpy V-notch test data.

The present invention also provides for estimating the fracture toughness, $K_{Jic}$, of the structural material under test using the mechanical properties measured by the ABI test and the following equation:

$$K_{Jic} = a(\sigma_y \cdot n \cdot E_2 \cdot L^*)^{0.5} \tag{15}$$

where a is a material-type constant, $\sigma_y$, n, and $E_2$ are as defined above and measured from ABI tests, and $L^*$ is the characteristic distance ahead of a crack tip over which the strain must exceed a critical fracture value ($\epsilon_f$) in order for ductile fracture to occur. Empirically calibrated values for the characteristic distance, $L^*$, for each class of material are stored in the computer (e.g. a value of 350 μm is reported for pressure vessel steel A533 grade B, class 1). Equation (15) is a simplification of prior art. A modified critical strain model used to estimate fracture toughness from tensile test data was reported in an article co-authored by the inventor and published by ASM as described earlier. The simplification to this work involved the use of the strain-hardening exponent, n, instead of the tensile uniform elongation. Furthermore, the use of Equation (15) provides a nondestructive and localized means to estimate and map the changes in fracture toughness from ball indentations performed on a deformed or aged metallic structure in the field. Such a fracture toughness evaluation is not possible by other means since standard fracture toughness measurements involve the destructive testing of large specimens.

The following Examples are provided to illustrate some of the methods of the invention and are not to be taken as limiting the scope of the invention which is defined by the appended claims.

EXAMPLE I

The estimation of fracture toughness from automated ball indentation (ABI) data was demonstrated by conducting ABI tests on two broken halves of 25.4-mm-thick compact specimens of an alloy steel used widely in the manufacture of nuclear pressure vessels, namely A533 grade B class I steel. These specimens were tested previously according to ASTM Standard E-813-81. The ABI-derived values of n, $\sigma_y$ were used together with values of 206 GPa for the elastic modulus and 350 μm for $L^*$ to predict the fracture toughness using Equation (15). Table I shows the agreement between measured and ABI-estimated fracture toughness values; the difference of less than 11% is considered excellent for state-of-the-art fracture toughness determinations.

TABLE I

Comparison of Predicted (Using ABI Data) and Measured Fracture Toughness Values for A533B Class 1 Steel Tested at Room Temperature.

| Specimen Number | ABI Test DATA | | $K_{Jic}$ (MPa·m$^{0.5}$) | | |
| --- | --- | --- | --- | --- | --- |
| | Yield Strength (MPa) | n | A (Measured) | B (ABI-Predicted) | $\frac{B-A}{A}$ (%) |
| K52C | 400 | 0.187 | 198.5 | 220.3 | +11.0 |
| K53A | 407 | 0.173 | 234.1 | 213.8 | −8.7 |

TABLE I-continued

Comparison of Predicted (Using ABI Data) and Measured Fracture Toughness Values for A533B Class 1 Steel Tested at Room Temperature.

| Specimen Number | ABI Test DATA Yield Strength (MPa) | n | $K_{Jic}$ (MPa.m$^{0.5}$) A (Measured) | B (ABI-Predicted) | $\frac{B-A}{A}$ (%) |
|---|---|---|---|---|---|
| Average: | | | 216.3 | 217.1 | +0.4 |

EXAMPLE II

The automated ball indentation (ABI) portion of the present invention was also demonstrated to evaluate its accuracy and applicability to irradiated materials testing. The ABI tests were conducted on A212B pressure vessel steel used in the fabrication of the vessel shell of the High Flux Isotope Reactor (HFIR) at the Oak Ridge National Laboratory. This material was chosen to be tested in both unirradiated and irradiated conditions for the following two reasons: (1) its apparent high embrittlement rate; and (2) the applicability of its embrittlement fleence-rate effect to the evaluation of the integrity of light-water reactor (LWR) pressure vessel supports.

As described above, cyclic loading and unloading of an indenter (a 1.59-mm diameter ball), was controlled by a computer (Hewlett-Packard) using software prepared for the invention. The applied loads and associated displacements (depth of penetration of the indenter into the test specimen at a given location) were measured during both loading and unloading using a load cell and a spring-loaded linear voltage differential transducer (LVDT) of conventional design but mounted on a head as shown in FIGS. 1 and 2. The increasing loads for the succession of loading cycles were provided by an MTS hydraulic testing machine. The data from the load cell and LVDT were received by a data acquisition system and processed by the computer to generate the true-stress/true-plastic-strain curve, and to calculate the yield strength and the strain-hardening exponent.

Figure 5:
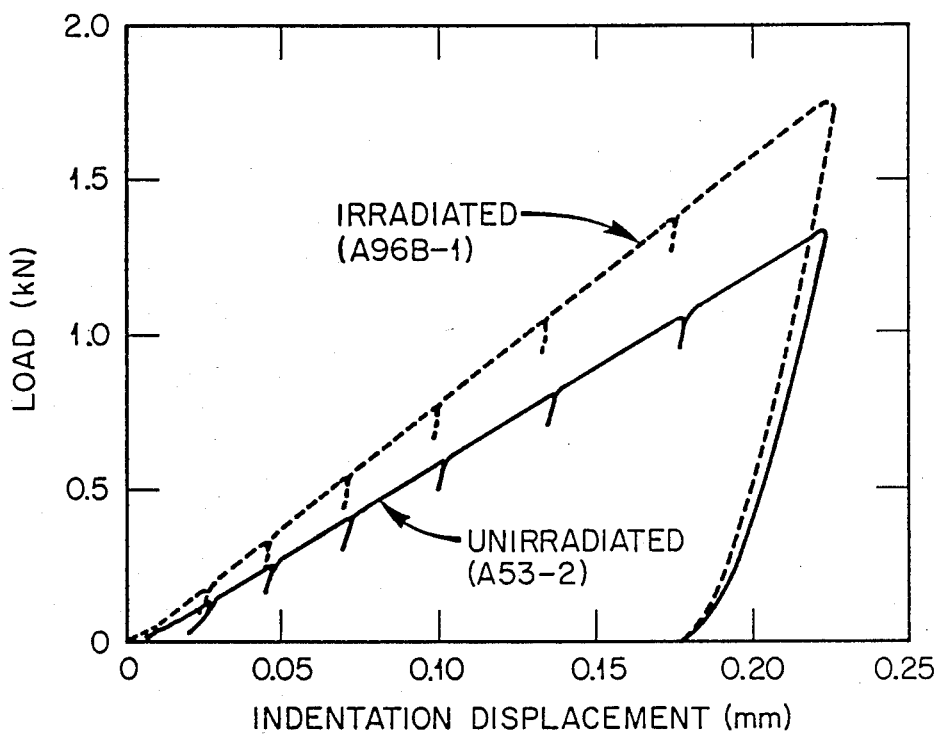
FIG. 5 is a graph showing sample Automated Ball Indentation (ABI) test results (load versus displacement using a 1.59-mm diameter ball indenter) on both unirradiated and irradiated A212B pressure vessel steel specimens.

FIG. 5 shows the load-versus-displacement curves of the unirradiated and irradiated specimens.

Figure 6:
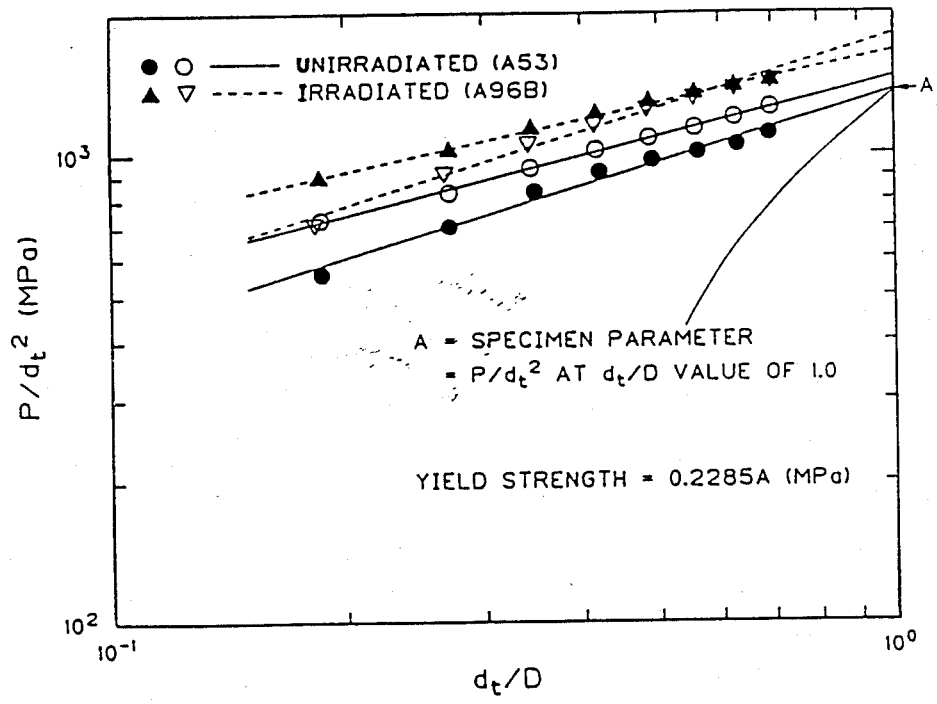
FIG. 6 is a graph showing yield strength results calculated from the entire ABI load-displacement curve for two tests of each material condition conducted on unirradiated and irradiated A212B pressure vessel steel specimens.
Figure 7:
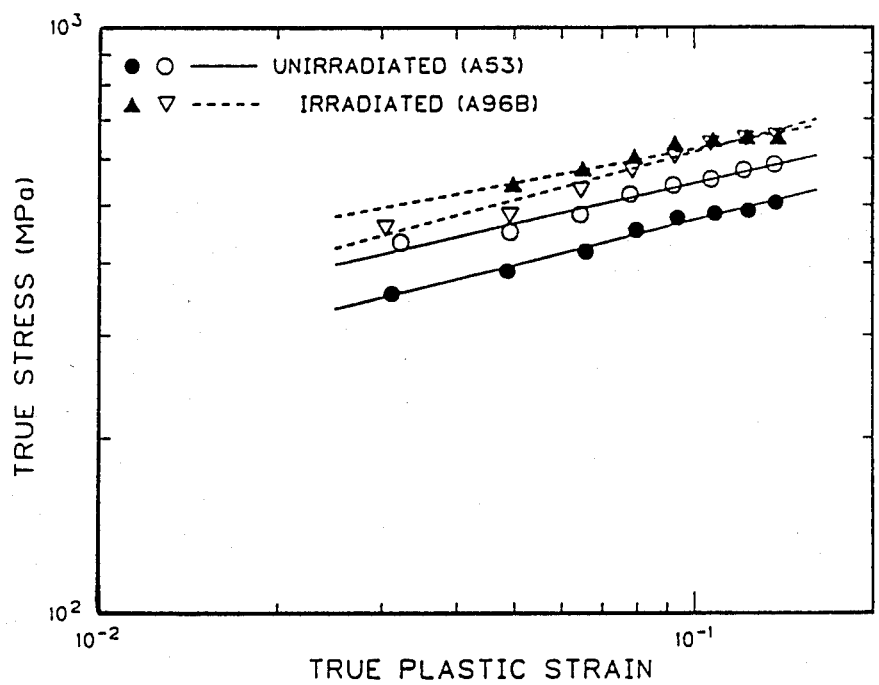
FIG. 7 is a graph showing flow properties measured from ABI tests on unirradiated and irradiated A212B pressure vessel steel specimens (note that each curve is entirely obtained from cyclic, incremental load indentation testing at a single penetration location).

FIG. 6 shows the yield strength results of two ABI tests of each material condition conducted on unirradiated and irradiated A212B steel specimens. The intersection of the log−log plot of $P/d_t^2$ versus $d_t/D$ with the vertical axis at $d_t/D = 1.0$ determined the test material parameter A of Equation (11). Multiplying this value by the aforementioned constant ($\beta_m = 0.2285$), of Equation (12) determined the yield strength of the test material. Using the ABI test data, the true-stress/true-plastic-strain curve was determined for the two types of specimens, with the results plotted in FIG. 7.

A comparison of yield strength values measured using both the ABI and conventional tensile tests performed on the same material condition is shown in Table II. This table shows that the difference between the average values of yield strength measured by these two different methods was less than 2%.

TABLE II

Comparison of Yield Strength Results Measured by Uniaxial Tensile and ABI tests on A212B Steel

| | Uniaxial Tensile | | | Automated Ball Indentation | | | |
|---|---|---|---|---|---|---|---|
| Fluence, >1 MeV (n/cm$^2$ × 10$^{17}$) | Specimen Number | Yield Strength (MPa) | Average (A) | Specimen Number | Strength (MPa) | Average (B) | $\frac{B-A}{A}$ (%) |
| 0.0 | A59-HA-15 | 336 | | A53-3 | 333 | | |
| 0.0 | A59-HA-1 | 318 | 329 | A53-2 | 312 | 323 | −1.8 |
| 0.0 | A59-HA12 | 333 | | | | | |
| 0.12 | A31-3 | 333 | | A31B-1 | 340 | | |
| 0.12 | A31-4 | 334 | 329 | A31B-7 | 325 | 333 | +1.2 |
| 0.12 | A31-1 | 331 | | | | | |
| 0.12 | A31-2 | 318 | | | | | |
| 1.53 | A96-4 | 396 | | A96B-2 | 410 | | |
| 1.53 | A96-2 | 373 | 389 | A96B-1 | 377 | 394 | +1.3 |
| 1.53 | A96-1 | 394 | | | | | |
| 1.53 | A96-3 | 392 | | | | | |

Figure 8:
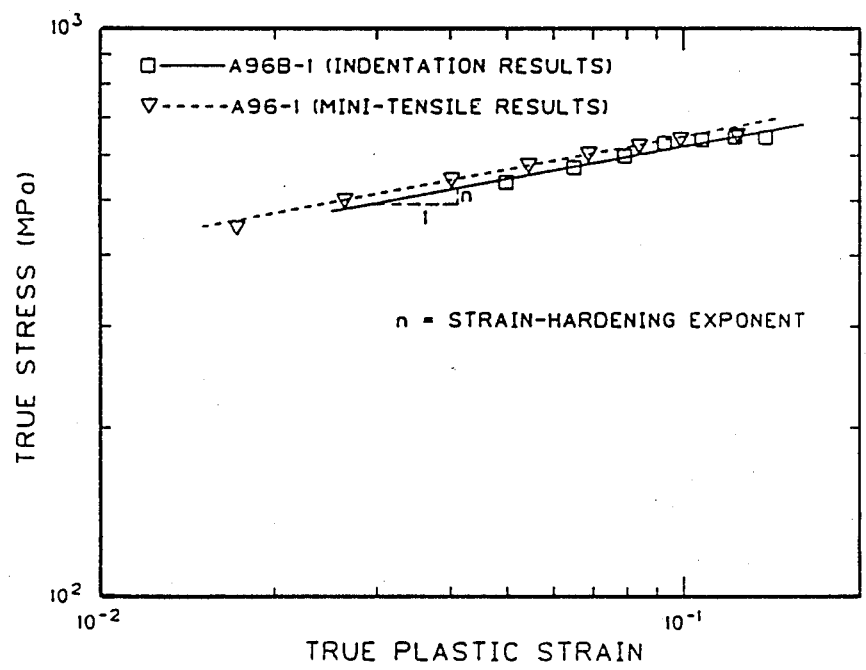
FIG. 8 is a graph showing a comparison between flow properties (true-stress/true-plastic-strain curve) measured from ABI and uniaxial tensile tests on irradiated A212B pressure vessel steel.

The true-stress/true-plastic-strain curve for the irradiated material (taken from HFIR irradiation surveillance specimens) as obtained from ABI data and tensile test data is plotted in FIG. 8. The slope of the respective curves is the strain-hardening exponent, n. For these ABI and tensile tests, the values of n were 0.192 and 0.195, respectively. Again, the ABI data showed excellent agreement with the tensile test data; thus demonstrating that the in-the-field testing using the present invention will provide accurate information about structural components (whether irradiated or not) using the field indentation microprobe (FIM) of this invention.

From the following it will be recognized by those versed in the art that a novel device, and its unique method of operation, have been provided for the in-the-field determination of mechanical and physical properties of a structure. The device of this invention will be of value where data are needed to be derived in the field so as to measure the flow properties and fracture toughness and crack sizes and thus to determine the integrity of a structure. (The combination of fracture toughness property and critical crack size determines the allowable service loads or stresses.) The testing is accomplished usually in a nondestructive manner. The device will be of particular use to nondestructively test structures after extensive use or, for example, to determine whether useful service life can be extended for such structures as a nuclear pressure vessel, an aircraft, a submarine, etc. Also tests can be made after misuse or damage. This device can be inserted inside a vessel, for example, as with the use of a robot. While the device is intended primarily for metallic structures, it can be adapted for other materials through the use of minor modifications and appropriate software. Also, by using a cylindrical indenter with a flat tip, creep tests of a material can be performed. While devices of the prior art are restricted to measuring only hardness which might be approximately related to ultimate tensile strength, the present invention provides information as to elastic (Young's) modulus, yield strength, true-stress/true-plastic-strain curve, strain-hardening exponent, strength coefficient, Lüders strain, shift in the ductile-to-brittle transition temperature for steel plates and welds, fracture toughness, presence and orientation of residual stresses, component thickness, and crack size.

Figure 9:
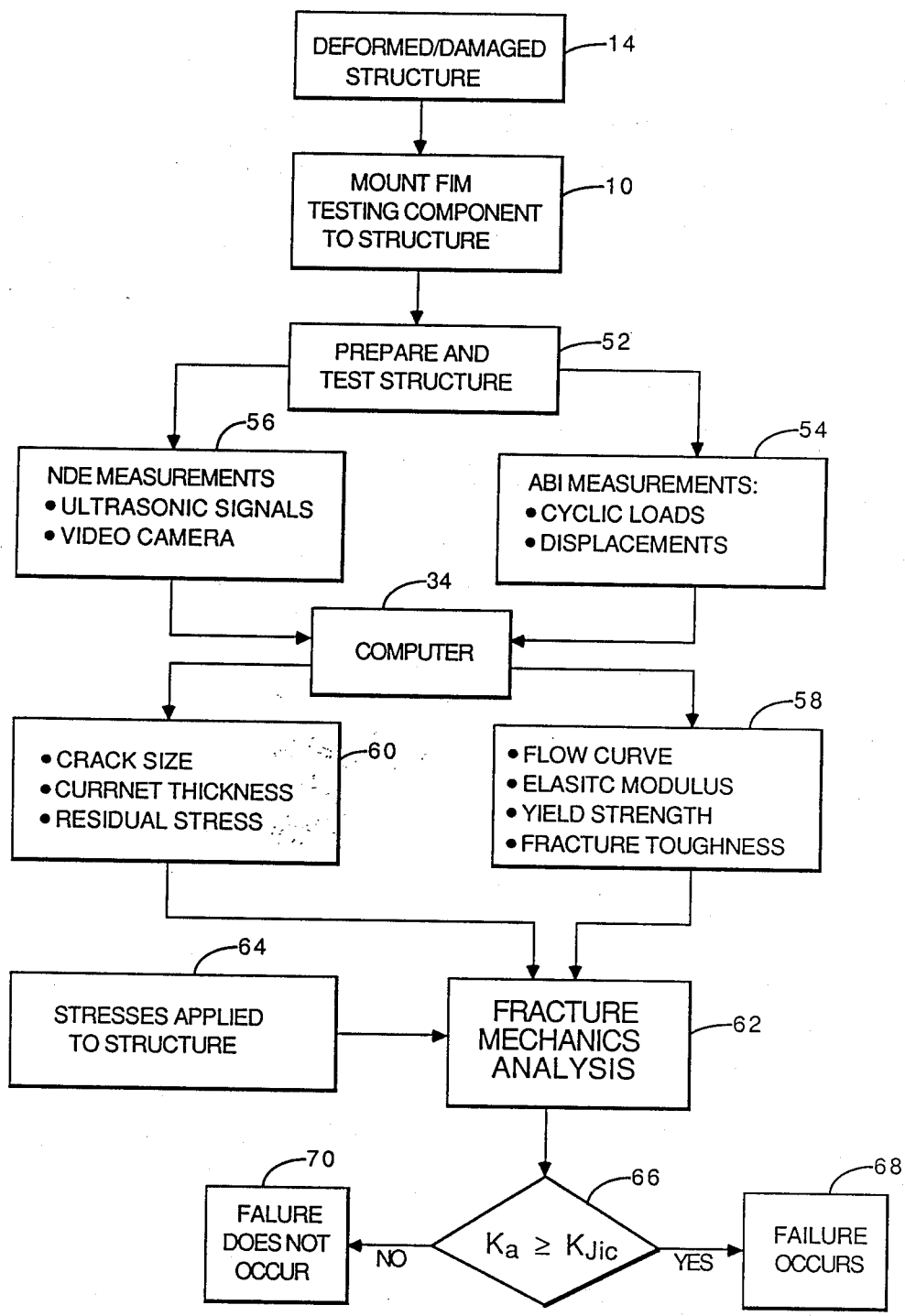
FIG. 9 is a flow diagram of the processes of the Field Indentation Microprobe (FIM) apparatus for measuring the mechanical and physical properties and for evaluating the integrity of a structure on the basis of these measurements.

The advantages and ultimate objectives of the invention will be best understood from the flow chart of FIG. 9. A deformed/damaged structure 14 (e.g. a pressure vessel or a tank car) is evaluated by securely attaching the testing head of the FIM apparatus 10 to the area of interest or concern. At a selected location, (box 52), preparation is performed by cleaning and polishing the structure surface and then two types of testing are conducted, namely, the nondestructive evaluation (NDE), and the mechanical testing using the Automated Ball Indentation (ABI) technique. The NDE measurements (box 56) using the ultrasonic transducers are analyzed using the computer 34 to calculate the crack size and current material thickness, and indicate residual stress presence and orientation (box 60). Similarly, the ABI measurements (box 54) are analyzed using the computer 34 to calculate the flow properties ($\sigma_t-\epsilon_p$ curve), strain-hardening exponent, elastic modulus, yield strength, and fracture toughness (box 58). At location or box 62 of FIG. 9, a person who is in charge of conducting the FIM tests and performing the fracture mechanics analysis uses the information from box 60 (crack size, structural geometry, component current thickness, etc.) and the information from box 64 (the loads or stresses to be applied to the structure) to calculate the applied stress intensity factor ($K_a$). The fracture toughness, $K_{Jic}$, calculated from the ABI data in box 58 is then compared to $K_a$ at 66. If the value of $K_a$ is greater than or equal to the critical value $K_{Jic}$ (a "yes" answer for the logic of 66), then subsequent failure under service-related loading will occur (box 68). The "no" answer for the logic of 66 indicates that failure of the structure will not occur (box 70). For cases where the failure mechanism for other structures is by plastic yielding then the logic of 66 should be to compare the applied stress to the yield stress.

Although the invention has been described with typical illustrations of components, there is no intent to limit the invention by these illustrations. Rather, the invention is to be limited only by the appended claims or their equivalents when read together with the detailed description.

Thus having illustrated and described my invention, what I claim is:

1. An indentation microprobe apparatus for automatically and nondestructively determining mechanical and physical properties of a structure in the field, which comprises:

a head member adapted for movement in X and Y directions in a plane substantially parallel to a surface of said structure;

attaching means for releasably attaching said head member rigidly to said surface of said structure;

load applying means operatively associated with head member and said attaching means;

a load measuring means mounted to said head member having an axis substantially perpendicular to said surface of said structure, said load measuring means adapted to provide an output signal in proportion to load applied and released to said structure by said load applying means;

at least one indenter holder carried by said load measuring means and adapted for axial movement along said axis of said load measuring means, said indenter holder having an exposed end;

at least one indenter carried by said exposed end of said holder, said indenter having a selected configuration and size;

a displacement transducer means mounted on said load measuring means, said displacement transducer means adapted to provide an output signal in proportion to movement of said indenter into and out of said surface of said structure;

a data acquisition system for receiving said output signal from said load measuring means and said output signal from said displacement transducer means, at least one ultrasonic transducer means carried by said load cell means toward said surface, said ultrasonic transducer means adapted to provide an output signal in proportion to thickness and/or crack size of said metallic structure;

a video camera means carried by said head member for viewing said surface proximate said ball indenter and for measuring the final plastic diameter of an indentation produced in said surface by said ball indenter; and computer means, including pre-selected computer programs, operatively coupled to said load applying means via said data acquisition system to automatically and cyclically and incrementally apply and release selected increasing loads, at a specified strain rate, to said indenter holder and, thus, to said indenter for making multiple impressions, at a given single location on said surface, feedback of direct data or data from subsequent calculations is used as applicable for test operation control in conjunction with said pre-selected computer programs, and to analyze data received by said data-acquisition system during said cyclic application and release of said loads to calculate, according to the principles and relationships of elastic or plastic material behavior or both, the true-stress/true-plastic-strain curve, the strain-hardening exponent, the strength coefficient, the elastic modulus, the yield strength, Lüders strain, shift in the ductile-to-brittle transition temperature, and the fracture toughness of said structure at said given location, and to evaluate the integrity of said structure utilizing said measured mechanical and physical properties.

2. The microprobe of claim 1 whereby, said ultrasonic transducer means is adapted to provide an output signal in proportion to thickness or crack geometry or both of said structure at inspection location, said output signal being provided to said data acquisition system for analysis utilizing the computer means to determine the material pile-up around indentation, presence and orientation of residual stresses, and crack size of said structure.

3. The microprobe of claim further comprising a tool unit carried by said load measuring means toward said surface for preparing said surface prior to said movement of said indenter into said surface and prior to ultrasonic, inspection of said structure.

4. The microprobe of claim 1 wherein said indenter is a ball indenter.

5. The microprobe of claim 1 further comprising magnetic and/or optical media operatively associated with said computer means for storing test data and results, said computer means further comprising printer and/or plotter means for visually displaying tests results.

6. The microprobe of claim 1 wherein said load measuring means is a load cell.

7. An indentation microprobe for the automated measurements of mechanical and physical properties of a metallic structure in the field, which comprises:
 a head member adapted for movement in X and Y directions in a plane substantially parallel to a surface of said metallic structure;
 attaching means for releasably attaching said head member rigidly to said surface of said metallic structure;
 load applying means operatively coupled to said head member and said attaching means;
 a load cell means mounted to said head member, said load cell means having an axis substantially perpendicular to said surface of said metallic structure, said load cell means adapted to provide an output signal corresponding to a load applied and/or released to said metallic structure by said load applying means;
 an indenter holder carried by said load cell means and adapted for axial movement along said axis of said load cell means, said indenter holder having an exposed end;
 a ball indenter carried by said exposed end of said holder, said ball indenter having a selected diameter;
 a displacement transducer means mounted on said load cell means, said displacement transducer means adapted to provide an output signal in proportion to movement of said indenter into and out of said surface of said metallic structure;
 at least one ultrasonic transducer means carried by said load cell means toward said surface, said ultrasonic transducer means adapted to provide an output signal in proportion to thickness and/or crack size of said metallic structure;
 a video camera means carried by said head member for viewing said surface proximate said ball indenter and for measuring the final plastic diameter of an indentation produced in said surface by said ball indenter;
 a data acquisition system for receiving said output signals from said load cell means, said ultrasonic transducer means and said displacement transducer means; and
 a computer means, including pre-selected data processing and control programs, operatively coupled to said load applying means via said data acquisition system to automatically and cyclically and incrementally apply and release loads, at a specified strain rate, to said indenter holder and thus, to -aid indenter at a given single location on said surface, feedback of direct data or data from subsequent calculations is used as applicable for test operation control in conjunction with said pr-e-selected computer programs, and to analyze data received by said data acquisition system during said cyclic application and release of said loads to calculate, according to the principles and relationships of elastic or plastic material behavior or both, the true-stress/true-plastic-strain curve, the strain-hardening exponent, the strength coefficient, the elastic modulus, the yield strength, Lüders strain, the shift in the ductile-to-brittle transition temperature for steel plates a-d welds, and the fracture toughness of said metallic structure at said given location, and to evaluate the integrity of said metallic structure utilizing said measured mechanical and physical properties.

8. The microprobe of claim 7 wherein said attaching means is a multilegged support for mounting said axis of said load cell means substantially perpendicular to said surface.

9. The microprobe of claim 7 further comprising a tool unit carried by said load cell means toward said surface for preparing said surface prior to said movement of said ball indenter into said surface and prior to ultrasonic inspection of said structure.

10. The microprobe of claim 7 further comprising a magnetic and/or optical media operatively associated with said computer means for storing test data and results, said computer means further comprising printer and/or plotter means for visually displaying said test results provided by said computer means as to said mechanical and physical properties of said metallic structure.

11. The computer means of claim 7 further comprising program-specified test operating limits related to interim and final indenter displacement, and maximum indenter load.

12. The computer means of claim 7 further comprising program-specified operating procedure for positioning and operating the ultrasonic transducers of said testing head of said indentation microprobe.

13. An indentation microprobe for automatically and non-destructively determining mechanical properties of a structure in the field, which comprises:
 a head member adapted for movement in X and Y directions in a plane substantially parallel to a surface of said structure;
 attaching means for releasably attaching said head member rigidly to said surface of said structure;
 load applying means operatively associated with said head member and said attaching means;
 a load measuring means mounted to said head member having an axis substantially perpendicular to said surface of said structure, said load measuring means adapted to provide an output signal of load applied to said structure by said load applying means;
 an indenter holder carried by said load measuring means and adapted for axial movement along said axis of said load measuring means, said indenter holder having an exposed end;
 an indenter carried by said exposed end of said holder, said indenter having a selected size and configuration;
 a displacement transducer means mounted on said load measuring means, said displacement transducer means adapted to provide an output signal in proportion to movement of said indenter into said surface of said structure;

a data acquisition system for receiving said output signal from said load cell and said output signal from said displacement transducer means; and computer means, including pre=selected computer programs, connected to said load applying means through said data acquisition system to automatically and cyclically apply and release selected increasing loads to said indenter holder, and, thus, to said indenter, at a given position on said surface, and to analyze data received by said data acquisition system during said cyclic application and release of said loads to compute and produce an information signal corresponding to said mechanical properties of said structure at said given position.

* * * * *